(12) United States Patent
Davis et al.

(10) Patent No.: US 6,179,827 B1
(45) Date of Patent: Jan. 30, 2001

(54) CATHETER HAVING INTEGRAL EXPANDABLE/COLLAPSIBLE LUMEN

(75) Inventors: Albert Davis; Mitta Suresh, both of Richardson, TX (US)

(73) Assignee: Chase Medical, Richardson, TX (US)

( * ) Notice: Under 35 U.S.C. 154(b), the term of this patent shall be extended for 0 days.

(21) Appl. No.: 09/204,108

(22) Filed: Dec. 1, 1998

Related U.S. Application Data

(60) Provisional application No. 60/078,087, filed on Mar. 16, 1998.

(51) Int. Cl.$^7$ .................................................. A61M 29/00
(52) U.S. Cl. ........................... 604/523; 604/532; 604/96
(58) Field of Search ................................ 604/96, 98, 100, 604/101, 103, 508, 509, 523, 532, 533, 534

(56) References Cited

U.S. PATENT DOCUMENTS

| | | | |
|---|---|---|---|
| 4,406,656 | 9/1983 | Hattler et al. | 604/280 |
| 5,383,854 * | 1/1995 | Safar et al. | 604/98 |
| 5,462,530 | 10/1995 | Jang | 604/160 |
| 5,466,222 | 11/1995 | Ressemann et al. | 604/96 |
| 5,536,250 * | 7/1996 | Klein et al. | 604/102 X |
| 5,618,267 | 4/1997 | Palestrant | 604/53 |
| 5,738,649 * | 4/1998 | Macoviak | 604/509 X |
| 5,795,331 * | 8/1998 | Cragg et al. | 604/509 X |

\* cited by examiner

Primary Examiner—John D. Yasko
(74) Attorney, Agent, or Firm—Jackson Walker, LLP

(57) ABSTRACT

A catheter and method of use as an aortic balloon catheter having an integral expandable/collapsible lumen. The catheter comprises a main catheter body having a plurality of lumens extending therethrough, and further includes an expandable/collapsible lumen disposed thereabout and carried by the main catheter body. The expandable/collapsible lumen has a relatively large diameter when inflated with respect to the main catheter body, and is self-inflating by fluid pressure when the fluid flows therethrough. The large inflatable/collapsible lumen is attached at its distal end to the main catheter body and thus is carried therewith into a body vessel, and thus is also supported by the catheter body to avoid kinking. The catheter of the present invention is ideally suited for insertion into smaller access arteries for placement into larger arteries, such as an aortic balloon catheter which can be inserted into a smaller femoral artery and advanced into the ascending aorta to provide arterial return of oxygenated blood into the ascending aorta. The catheter further has an adjustable length. The present invention also achieves technical advantages as a catheter for insertion into any body vessel having a limited diameter and which is susceptible to trauma, such as a urethra.

20 Claims, 4 Drawing Sheets

CATHETER HAVING INTEGRAL EXPANDABLE/COLLAPSIBLE LUMEN

This application claims benefit to Application Ser. No. 06/078,087, filed Mar. 16, 1998.

FIELD OF THE INVENTION

The present invention is generally related to medical catheters and procedures for using the same, and more particularly to catheters having multiple lumens adapted to be inserted into body vessels including access vessels having a limited diameter with respect to the cannula diameter.

BACKGROUND OF THE INVENTION

In the medical profession, the use of catheters to deliver and vent fluids from body vessels is becoming more pervasive due to the advancement of minimally invasive procedures. It is often desired to insert a catheter into a body vessel such as the aorta, urethra etc. via an access vessel having a restricted diameter. The catheter usually has a plurality of lumens, for instance, one lumen to infuse a fluid such as a medicant or oxygenated blood, and another lumen for inflating a balloon to selectively occlude the body vessel. The number of lumens, and particularly the aggregate cross sectional area of the lumens, substantially determines the overall catheter diameter. It is desired to keep the overall diameter of the catheter as small as possible, especially with respect to the access vessel and the vessel for which it is intended to be placed to reduce trauma to the vessel.

With respect to aortic balloon catheters in particular, these catheters may be percutaneously inserted into a patient's femoral artery, serving as an access vessel, and advanced upwardly into the aorta of the patient. According to one conventional method, a first catheter is inserted into the femoral artery and advanced into the ascending aorta. The catheter may include a balloon for selectively occluding the aorta and have multiple lumens terminating at the distal end thereof for delivering cardioplegia to the aortic root and/or venting fluid from the aorta above the aortic root. Other lumens may provide for instrumentation to be inserted into the aorta, which may be advanced through the aortic valve into the heart. The proximal end of the catheter may be provided with a lumen terminating proximate the point of insertion to provide arterial return of oxygenated blood. Alternatively, a separate second catheter may be inserted into the patient's other femoral artery to provide arterial return of oxygenated blood. This second catheter is used to reduce the overall diameter of the first catheter body advanced into the aorta, thus reducing trauma to the aorta lining. The distal end of this second catheter is also advanced only to proximate the point of insertion since it is semi-rigid and has a relatively large diameter to provide the required arterial return of oxygenated blood into the aorta. By using a second catheter, a rather large diameter first catheter is not necessary to be inserted into the aorta which may cause trauma to the lining of the artery. However, returning oxygenated blood well below the aorta requires oxygenated blood to flow counter to typical arterial blood flow, upwardly into the ascending aorta to the various arteries branching therefrom.

The disadvantages of this approach include the fact that returning oxygenated blood to the aorta upwardly in a direction counter to normal flow has been found in some studies to be damaging to the artery lining, and which may create aortic dissection, aneurysms, and in some cases death. In addition, this method requires a second infusion catheter to be inserted and manipulated which can be cumbersome.

A semi-rigid catheter having a large lumen for providing arterial return of oxygenated blood, as well as having lumens for pressure sensing, cardioplegia delivery/venting, and balloon inflation, necessitates a relatively large aortic balloon catheter having a large overall diameter that is difficult to femorally insert and manipulate up into the ascending aorta. If too large a catheter is used, the artery can be damaged or traumatized during insertion. It is desired to provide an improved catheter suited for use in body vessels having a limited diameter while being capable of delivering fluids at a high flow rate, two criteria that typically limit each other. In particular, the improved catheter would have one intended use as a catheter that can be femorally inserted to provide arterial return of oxygenated blood into the ascending aorta.

SUMMARY OF THE INVENTION

The present invention achieves technical advantages as a single catheter having a relatively large inflatable/collapsible lumen suited for insertion via smaller access vessels into larger vessels. The larger lumen is collapsed during insertion, and inflated during fluid delivery. The catheter can be inserted via an access artery and provide arterial return of oxygenated blood into the ascending aorta. This inflatable/collapsible lumen is secured to the main catheter body distal end, and surrounds the main catheter body having multiple lumens for facilitating other functions, such as pressure sensing at the catheter distal end, balloon inflation, and delivery of cardioplegia/venting at the catheter distal end.

In one embodiment, the catheter of the present invention derives technical advantages as being adapted to be percutaneously positioned into the aorta via a femoral artery with the large lumen in the collapsed position. This large lumen has a very thin wall facilitating inflation/collapsing about the main catheter body, preferably being comprised of polyethylene. Subsequently, by infusing a fluid, such as oxygenated blood, into the large lumen, the large lumen self expands due to fluid pressure of the fluid flowing therethrough to the lumen distal end. In another embodiment, the catheter can be inserted into other access vessels such as a subclavian artery.

The present invention derives technical advantages as a single catheter having multiple lumens and a reduced overall diameter. The catheter has a relatively small overall diameter during insertion through access arteries to the aorta with the large lumen in the collapsed position during advancement. This small diameter provides good control of the catheter during insertion, reducing the risk of damaging or traumatizing the lining of the artery. The catheter main body provides advancement of the large lumen within the vessel, and the catheter is sufficiently rigid to avoid kinking during insertion.

The present invention has other numerous uses and advantages in the surgical field whereby a large catheter lumen is required for exchanging a fluid to a body vessel, but the body vessel has a relatively small diameter and is difficult to navigate in and is susceptible to trauma. For instance, the present invention is ideally suited for use as a ureter catheter as well.

DESCRIPTION OF THE PREFERRED EMBODIMENT

Figure 1:
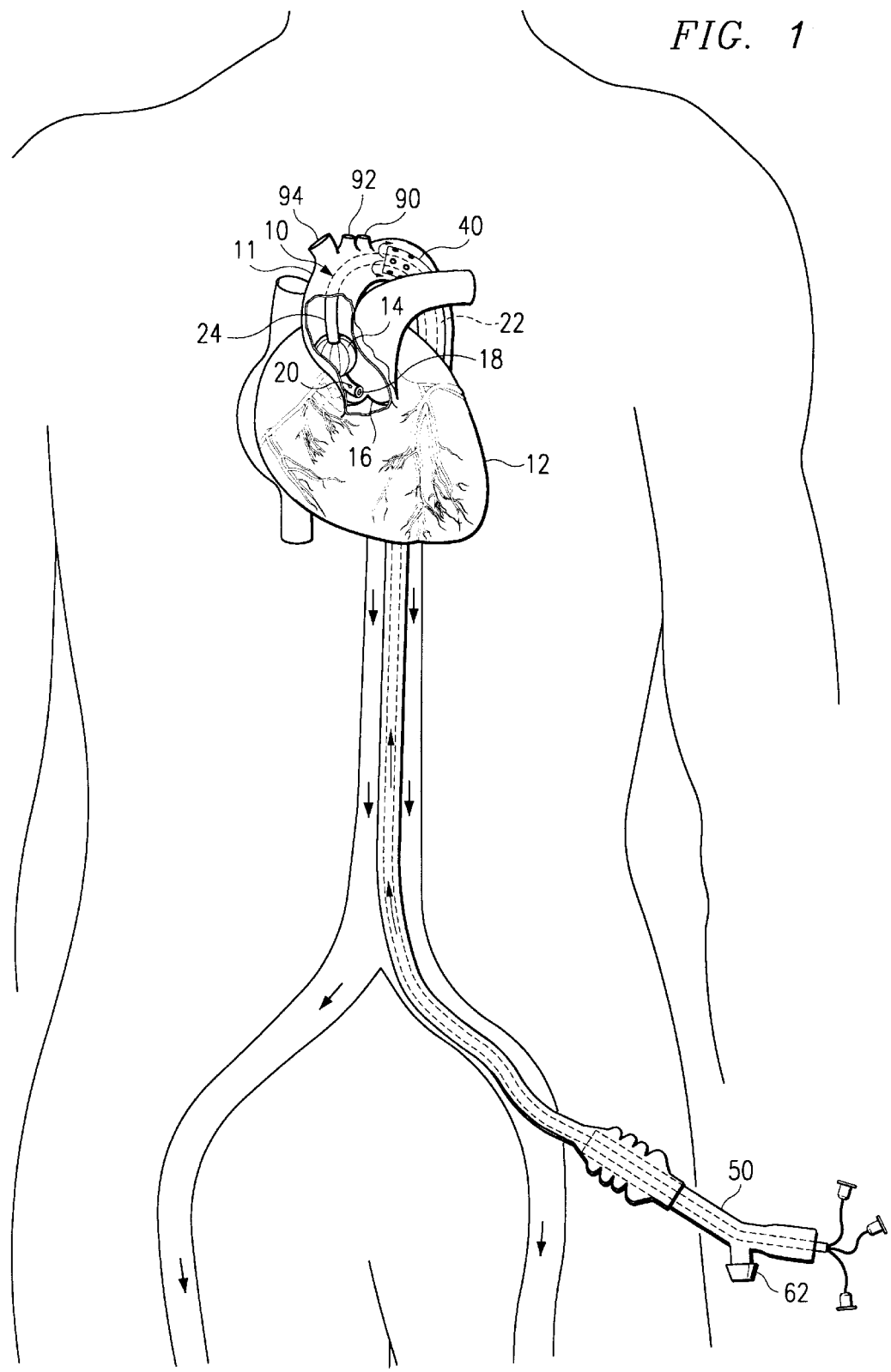
FIG. 1 is a perspective view of the catheter of the present invention shown femorally inserted into the aorta to provide arterial return of oxygenated blood when the catheter is used as an aortic catheter, wherein the large inflatable lumen is in the collapsed position during insertion to minimize trauma to the arteries and then inflated during delivery of oxygenated blood.

Referring now to FIG. 1, there is shown generally at 10 a catheter according to the preferred embodiment of the present invention used as an aortic balloon catheter femorally inserted into a patient and advanced into an ascending aorta 11 of a heart 12. Catheter 10 is seen to have a balloon member 14 positioned and expanded within the ascending aorta 11 to occlude the aorta above an aortic valve 16. Catheter 10 is further seen to include a cardioplegia delivery/venting port 18 and a pressure sensing port 20. Both ports 18 and 20 are defined distal of the balloon 14 for use within the ascending aorta above the aortic valve 16. Catheter 10 is further seen to include a large integral expandable/collapsible lumen 22 defined between a main catheter body 24 and a thin-walled sleeve 40 disposed about and carried by the main catheter body 24. Lumen 22 terminates proximate the distal end of the catheter 10, but proximal the balloon member 14. Lumen 22 is ideal for providing arterial return of oxygenated blood to the ascending aorta from an extracorporeal pump (not shown).

The present invention derives technical advantages as a catheter having a large lumen 22 that can be collapsed when inserted through a smaller access artery, such as the femoral artery, and into the ascending aorta. The catheter has a reduced overall diameter during insertion, thereby reducing trauma to the artery and improving control during insertion. The fluid pressure of the oxygenated blood delivered through lumen 22 causes member 40 to self expand from a collapsed state within the artery, whereby the diameter of the large lumen 22 is sufficient to provide oxygenated blood at a sufficient rate and pressure to perfuse the human body. As shown, a single catheter 10 is suitable for providing multiple functions during aortic perfusion, without requiring a second catheter and minimizing damage to the lining of the aorta.

Figure 2:
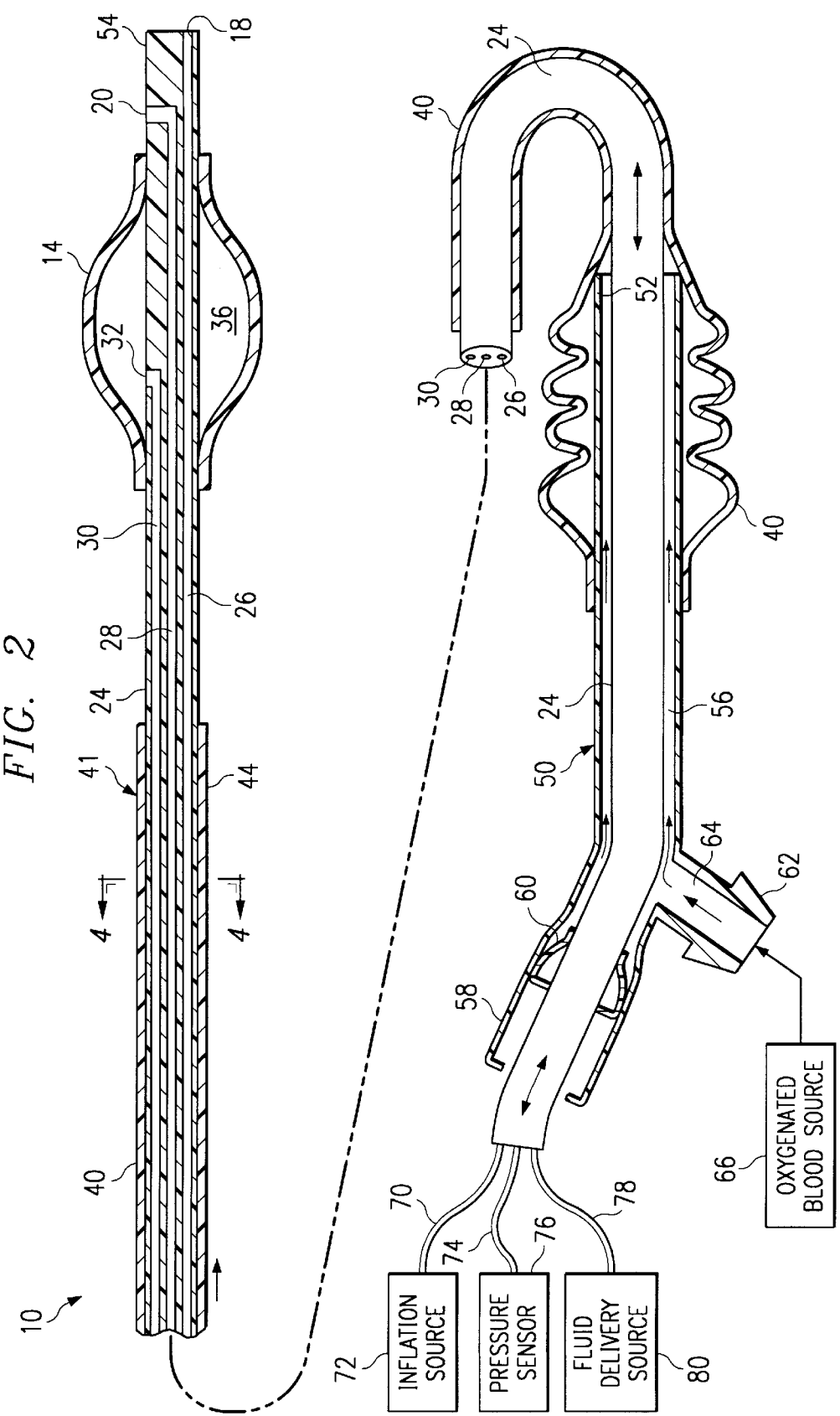
FIG. 2 is a longitudinal cross section of the catheter of the present invention shown in FIG. 1 including the large inflatable/collapsible lumen shown in the collapsed state as carried by the catheter body for advancement into a body vessel, such as for the procedure shown in FIG. 1.
Figure 3:
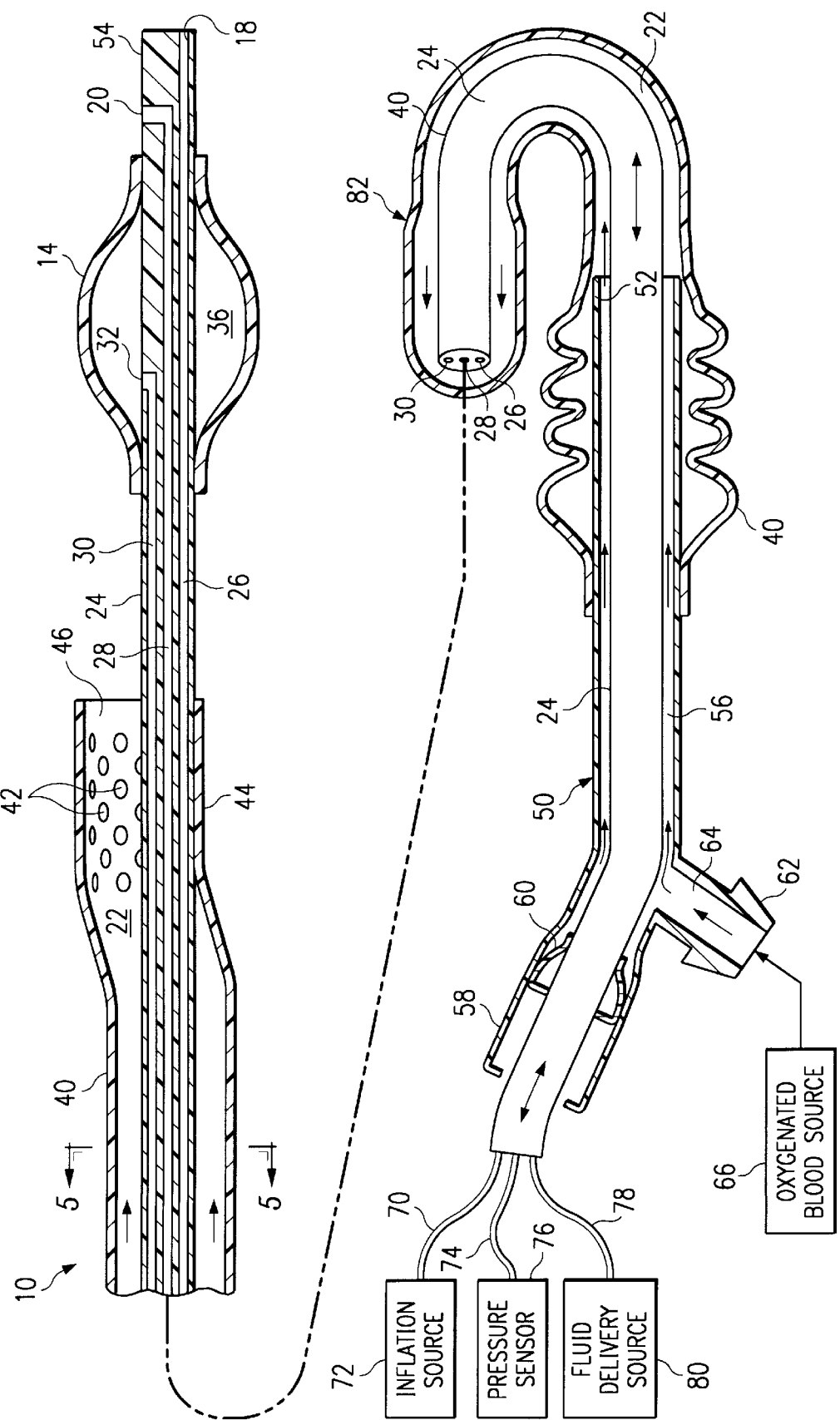
FIG. 3 is a longitudinal cross section of the catheter of FIG. 1 illustrating the large lumen in the expanded state when fluid flows therethrough into the body vessel.
Figure 4:
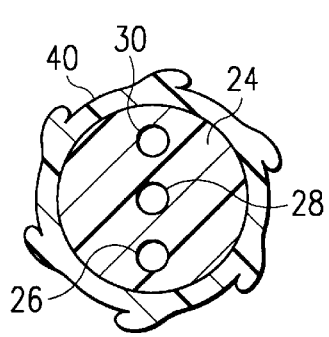
FIG. 4 is a transverse cross-section of the catheter taken along line 4—4 in FIG. 2 with the large lumen in the collapsed state.
Figure 5:
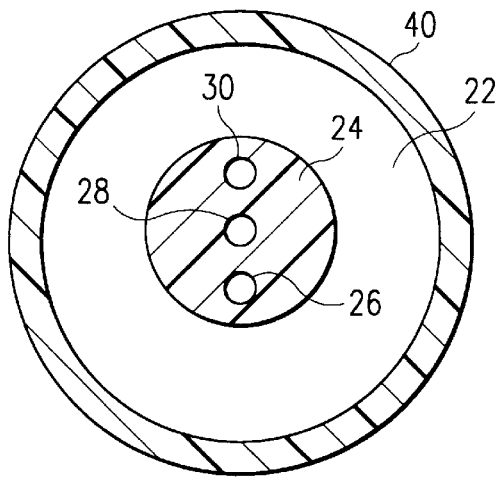
FIG. 5 is a transverse cross-section of the catheter taken along line 5—5 in FIG. 3 with the large lumen in the expanded state.

Referring now to FIG. 2 and FIG. 3, there is shown a longitudinal cross section of catheter 10 according to the preferred embodiment of the present invention. Sleeve member 40 is illustrated in the collapsed state in FIG. 2, and in the expanded state in FIG. 3. A transverse cross-section of catheter 10 having the member 40 in the collapsed state taken along line 4—4 in FIG. 2 is shown in FIG. 4. A transverse cross-section of catheter 10 having the member 40 in the expanded state taken along line 5—5 in FIG. 3 is shown in FIG. 5. It is noted again that the catheter 10 of the present invention is ideally suited as an aortic balloon catheter, however, the catheter 10 has other intended uses as well, such as a ureter catheter, and limitation for use as an aortic balloon catheter as described with reference to FIG. 1 is not to be inferred.

Catheter 10 is seen to have the main catheter body 24 which may be comprised of a conventional material such as polyvinylchloride (PVC), polyurethane, and polyethylene, although limitation to these materials is not to be inferred as catheter body 24 can be comprised of elastomeric materials as well, such as silicone. Extending within catheter body 24 is a plurality of lumens including a first lumen 26 extending to distal port 18, a second lumen 28 extending to distal port 20, and third lumen 30 extending to a balloon inflation port 32 within balloon 14. Also shown is balloon 14 being sealingly disposed about the distal end of the catheter body 24 to form a cavity 36 therewithin. When used as an aortic perfusion catheter, aortic root pressure is sensed via lumen 28 and port 20 above the aortic root 16 to determine if the balloon 14 is properly occluding the aorta 11. Then, cardioplegia is delivered to the aorta proximate the aortic root 16 via the lumen 26 and port 18 while sensing pressure at the aortic root to maintain a pressure of about 50–100 mm Hg.

The integral expandable/collapsible lumen 22 is formed by the thin-walled flexible lumen member 40 secured about and carried by the main catheter body 24. Lumen member 40 is preferably secured only at the distal end thereof at 41, but may alternatively be secured along a line to the outer surface of the main catheter body 24, either intermittently or continuously along catheter body 24 if desired. Securing lumen member 40 to catheter body 24 ensures that the distal end of member 40 is carried with main body 24 of catheter 10 during insertion.

Lumen member 40 preferably has a plurality of circumferentially extending openings 42 disposed at the member distal end 44, whereby lumen 22 terminates at a distal lumen opening at 46. Lumen opening 46 and sidewall openings 42 facilitate infusing fluid out the distal end of the large lumen 22 when expanded by the fluid pressure. Advantageously, lumen member 40 has a very thin wall thickness to maintain a low profile when collapsed about catheter body 24, as shown in FIG. 2 and FIG. 4. The collapsed lumen member 40 is folded and wrapped about the catheter body 24 and heated during manufacturing to keep the member close to catheter body 24, as shown in FIG. 4, until unfolded when inflated. Member 40 has a wall thickness preferably in the range of 0.002 inches, and preferably less than 0.01 inches, and is preferably comprised of a strong and resilient material such as polyethylene. Thus, the relative thickness of member 40 is not drawn to scale in FIG. 2 and FIG. 3. However, other dimensions and other conventional materials can be utilized as well, and limitation to polyethylene is not to be inferred. For instance, PVC, and polyurethane are suitable as well. The material chosen for lumen member 40 could be the same as the catheter body 24 to facilitate a secure attachment thereto using conventional mechanical, chemical or thermal bonding techniques.

In the preferred embodiment of the present invention, the inner diameter of lumen 22 in the expanded position, as shown in FIG. 3 and FIG. 5, is substantially larger than the outer diameter of the main catheter body 24, such as a 4 to 1 ratio. For example, the inner diameter of expanded lumen 22 may be about 10.7 mm (32 fr.), and the outer diameter of main catheter body 24 may be about 2.7 mm (8 fr.), although limitation to these dimensions is not to be inferred. This expandable lumen 22 is ideal for delivering a fluid, such as oxygenated blood, at a large fluid rate, whereby the smaller lumens 26, 28 and 30 are rather small and suited for their intended use, such as previously discussed. The main catheter body 24 is comprised of a suitable material such that it will not kink or buckle during insertion into the intended body vessel, such as the aorta or urethra. If desired, one of the lumens, such as lumen 26, can be provided with a malleable guide wire to selectively provide rigidity to the catheter body 24 and aid insertion of catheter 10 into the intended body vessel.

Cessation of fluid flow from the pump (not shown) through the lumen 22 will cause the lumen member 40 to collapse about the catheter body 24. Removal of catheter 10 from the body vessel, generally after fluid flow through lumen 22 has ceased, will further constrict lumen member 40 to cause any remaining fluid in lumen 22 to be dispensed out the distal opening 46 of the lumen 22. The lumen member 40 having a very flexible and thin wall will collapse about catheter body 24 as forces from the body vessel compress the lumen member 40 into its collapsed position, thus facilitating the easy removal of catheter 10 from the body vessel. The reduced catheter diameter during withdrawal further reduces trauma to the body vessel, which is a further technical advantage of the present invention.

Still referring to FIG. 2 and FIG. 3, the proximal end of catheter 10 is seen to have versatile features that have additional technical advantages. Each patient has different physical attributes and dimensions, and thus, the catheter of the present invention can be adapted to have a sufficient length for use within each particular patient. The proximal end of catheter 10 is seen to have a substantially rigid tubular body member generally shown at 50. The proximal end of the thin wall lumen member 40 is seen to be disposed about and sealingly attached about the circumference of the body member 50 distal end shown at 52. Notably, the proximal end of the lumen member 40 is seen to be bunched together in an accordion or serpentine like arrangement. This allows the length of the lumen member 40 defined distal of the distal end 52 to be selectively adjusted along with the length of catheter body 24 slidably extending through body member 50, thereby allowing the physician to selectively adjust the length of the catheter from body member distal end 52 to the catheter distal end 54. As indicated by the arrows, the main catheter body 24 is seen to be longitudinally slidably adjustable within a flow passageway 56 extending within body 50. Main catheter body 24 can be selectively adjusted by the physician such that it can be extended or retracted through body member 50 and proximal end 58. To provide a sealed, fluid tight, lumen 56, the proximal end 58 of body member 50 has positioned therein a hemostasis valve 60 sealingly disposed about the main catheter body 24. Valve 60 is sealingly engaged against the inner wall of passageway 56 to prevent oxygenated blood 66 from back flowing through proximal end 58, and to provide friction holding catheter body 24 in place at the selected position. The main catheter body 24 is longitudinally and slidably adjustable through valve 60 by the physician.

A flanged connector 62 is seen to form a Y connection in combination with proximal end 58 and has a passageway 64 extending therethrough in fluid communication with passageway 56. An oxygenated blood source 66 is fluidly coupled to member 62 and provides oxygenated blood to the catheter 10 via the passageway 64, lumen 56, and ultimately to the expandable/collapsible passageway 22 for delivery to the artery via the opening 46 and openings 42. The proximal end of catheter 10 is seen to have extending therefrom three separate passageways, namely, a passageway 70 in fluid communication with lumen 30 and coupled to an inflation source 72, a passageway 74 in fluid communication with lumen 28 and coupled to a pressure sensor device 76, and a passageway 78 in fluid communication with lumen 26 and coupled to a fluid delivery source 80. Each passageway connects to a respective connector, as shown in FIG. 1.

The outer diameter of main catheter body 24 is significantly smaller than the outer diameter of passageway 56 extending through body member 50. This creates a sufficient passageway 56 about main catheter body 24 for oxygenated blood to be communicated therethrough as sufficient rate and pressure to perfuse the human body as shown in FIG. 1. It is noted that the outer diameter of passageway 56 is less than the diameter of passageway 22 formed by the fully inflated lumen member 40, and thus, the fluid pressure will be higher through passageway 56 than the fluid pressure within passageway 22 during use. However, the short catheter portion that the blood is at a higher pressure is relatively short in relation to the overall length of the catheter 10. Thus, the required pressure for the oxygenated blood source 66 is suitable for delivery of oxygenated blood to an artery of the body, such as the aorta illustrated in FIG. 1. As shown in FIG. 3, the diameter of the lumen member 40 between proximate body member 50 and a transition 82 is reduced with respect to the lumen member 40 distal of transition 82 as this portion and the body member distal end 52 typically are positioned in the smaller access artery. The body member 50 has sufficient strength to facilitate insertion into a smaller access artery.

Figure 6:
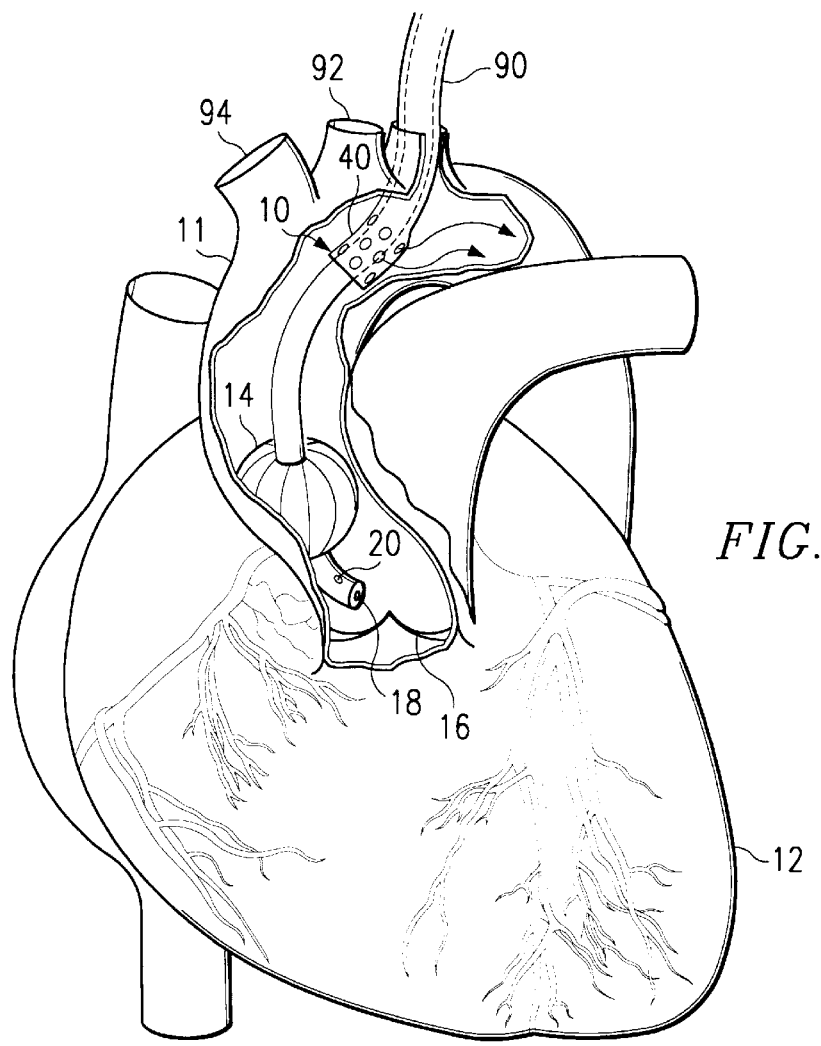
FIG. 6 is a view of the catheter of the present invention inserted into the aorta via the left subclavian artery.

Referring now to FIG. 6, there is shown an alternative preferred method of the use of the present invention whereby the catheter 10 is inserted into the ascending aorta via the left subclavian artery shown at 90. Like the femoral artery, the left subclavian artery can also be used as an access vessel for positioning the catheter 10 within the ascending aorta, as shown. The left subclavian artery, like the femoral artery, has a diameter less than the larger aortic artery and thus limits the overall diameter of the catheter that can be inserted therethrough. The present invention is ideal for insertion through small arteries for ultimate positioning within a larger artery, such as for the purpose of delivering fluids into the large artery at suitable flow rates while minimizing trauma to the arteries by the catheter.

It is intended that other arteries are suitable as access sites for the present invention as well, such as the left cartoid artery 92 and the right cartoid artery 94 as shown in FIG. 4. The desired insertion artery is left to the choice of the surgeon and will depend upon many criteria and will vary from patient to patient.

In summary, the present invention achieves technical advantages as a catheter which has the functional characteristics of a catheter having a predetermined outer diameter, but which during insertion and withdrawal has a smaller effective overall diameter. The present invention achieves advantages of a single catheter having multiple lumens, including a large inflatable lumen 22, which is suitable for insertion into smaller access arteries to reduce trauma to the arteries or blood vessels during insertion and withdrawal, while providing significant fluid flow therethrough to and toward the distal end of the catheter 10. The proximal end of the catheter has an adjustable length to allow the physician to adjust the length of the catheter during surgery to the particular patient.

Though the invention has been described with respect to a specific preferred embodiment, many variations and modifications will become apparent to those skilled in the art upon reading the present application. It is therefore the intention that the appended claims be interpreted as broadly as possible in view of the prior art to include all such variations and modifications.

We claim:
1. A catheter, comprising:
 a catheter body having a proximal end portion and a distal end portion; and a collapsible member disposed along at least a portion of said catheter body, said collapsible member having a distal end and defining a first lumen proximate said catheter body, said collapsible member being secured to said catheter body such that it can be advanced with said catheter body within a body vessel, wherein said collapsible member extends from said collapsible member distal end towards proximate said catheter body proximal end portion.

2. The catheter as specified in claim 1 wherein said collapsible member extends from said catheter body proximal end to proximate said catheter body distal end.

3. The catheter as specified in claim 1 further comprising a balloon member disposed about said catheter distal end portion, said catheter body having a second lumen communicating with the balloon for inflating said balloon.

4. The catheter as specified in claim 3 further comprising a third lumen extending through said catheter body and terminating at a port.

5. The catheter as specified in claim 4 further comprising a fourth lumen extending through said catheter body and terminating distal of said balloon member and between said third lumen port and said balloon.

6. The catheter as specified in claim 1 wherein said collapsible member comprises a sleeve with a thickness sufficiently thin such that said sleeve can be disposed against said catheter body.

7. The catheter as specified in claim 6 wherein said sleeve has substantially the same diameter as said catheter body when collapsed against said catheter body.

8. The catheter as specified in claim 7 wherein said sleeve has a wall thickness of less than about 0.01 inches.

9. The catheter as specified in claim 1 wherein said collapsible member is comprised of a first material and of a predetermined thickness such that fluid flow through said first lumen defined by said sleeve induces inflation of said collapsible member to define an increased diameter of said first lumen.

10. The catheter as specified in claim 6 wherein said sleeve is secured to at least one portion of said catheter body.

11. The catheter as specified in claim 10 wherein said sleeve is secured to said catheter body at a distal end of said sleeve.

12. The catheter as specified in claim 10 wherein said sleeve is secured along said catheter body from said sleeve proximal end to said sleeve distal end.

13. The catheter as specified in claim 1 wherein said collapsible member is comprised of polyethylene.

14. The catheter as specified in claim 1 further comprising a tubular body member, said catheter body being coupled to said tubular body member and being adjustable with respect to said tubular body member to adjustably establish a length of said catheter.

15. The catheter as specified in claim 14 wherein said catheter body is slidingly received within said tubular body member.

16. The catheter as specified in claim 15 wherein said tubular body member forms a passageway about said catheter body, said passageway being in fluid communication with said first lumen.

17. The catheter as specified in claim 15 wherein said collapsible member is connected to said tubular body member, wherein said collapsible member is adjustable in length with respect to said tubular body member.

18. The catheter as specified in claim 17 wherein said collapsible member is disposed about said tubular body member and is collapsible in the longitudinal direction with respect to said tubular body member.

19. A catheter comprising:
a catheter body having proximal portion and a distal portion; and
a collapsible member having a distal end and positioned along at least a portion of the catheter body and defining a lumen therein, the collapsible member expandable from a first collapsed condition to a second expanded condition in response to fluid flow through the lumen formed therein, said collapsible member extending from said collapsible member distal end towards proximate said catheter body proximal portion.

20. A catheter, comprising:
a catheter body having a proximal end portion and a distal end portion;
an expandable balloon member disposed on said catheter body; and
a collapsible member disposed along at least a portion of said catheter body, said collapsible member having a distal end and defining a first lumen proximate said catheter body, said collapsible member being secured to said catheter body such that it can be advanced with said catheter body within a body vessel, wherein said collapsible member extends proximal of said balloon towards said catheter proximal end portion.

* * * * *